US007454800B2

(12) United States Patent
Taylor et al.

(10) Patent No.: US 7,454,800 B2
(45) Date of Patent: Nov. 25, 2008

(54) ANATOMICALLY FITTED RESPIRATORY COMPONENT BELT

(75) Inventors: David S. Taylor, Accrington (GB); Peter D. Lee, Hartlepool (GB); Christopher P. Henderson, Brandon (GB)

(73) Assignee: 3M Innovative Properties Company, St. Paul, MN (US)

( * ) Notice: Subject to any disclaimer, the term of this patent is extended or adjusted under 35 U.S.C. 154(b) by 663 days.

(21) Appl. No.: 10/748,907

(22) Filed: Dec. 30, 2003

(65) Prior Publication Data

US 2005/0144706 A1 Jul. 7, 2005

(51) Int. Cl.
*A61M 15/00* (2006.01)

(52) U.S. Cl. ...................................... 2/338; 128/200.24

(58) Field of Classification Search ..................... 2/338, 2/236, 220, 235, 219, 300, 310–328, 920; 128/200.24, 201.23, 202.19, 95.1, 96.1, 97.1, 128/98.1, 99.1, 100.1, 101.1, 102.1, 876; 602/19, 32, 36, 38, 60, 61, 5
See application file for complete search history.

(56) References Cited

U.S. PATENT DOCUMENTS

| | | | | |
|---|---|---|---|---|
| 4,608,716 | A * | 9/1986 | Brumfield | 2/2.5 |
| 4,756,306 | A * | 7/1988 | Curlee | 602/19 |
| 5,009,225 | A * | 4/1991 | Vrabel | 128/201.24 |
| 5,052,603 | A | 10/1991 | Spina | |
| 5,105,806 | A * | 4/1992 | Woodhouse et al. | 128/96.1 |
| 5,394,870 | A | 3/1995 | Johansson | |
| 5,564,124 | A * | 10/1996 | Elsherif et al. | 2/69 |
| 5,609,283 | A | 3/1997 | Harrison, Jr. | |
| 5,728,055 | A | 3/1998 | Sebastian | |
| 5,833,095 | A | 11/1998 | Russell et al. | |
| 5,871,132 | A | 2/1999 | Hargreaves | |
| 6,038,747 | A | 3/2000 | Hamilton et al. | |
| 6,193,122 | B1 | 2/2001 | Buckley | |
| 6,199,736 | B1 | 3/2001 | Musarella et al. | |

(Continued)

FOREIGN PATENT DOCUMENTS

| | | |
|---|---|---|
| GB | 1588993 | 5/1981 |
| WO | WO 96/28065 | 9/1996 |
| WO | WO 02/056966 | 7/2002 |

OTHER PUBLICATIONS

3M Jupiter Comfort Belt, Part No. 022-25-03P4 (first sold in 2001).
Hornell AdFlo7 powered respirator and belt, www.hornell.com/Regional/0/products/adflo (printed Sep. 16, 2003).

*Primary Examiner*—Tejash Patel

(57) ABSTRACT

An anatomically fitted belt is used for carrying one or more waist-mounted respiratory protection components. The belt includes a main belt portion and a belt buckle portion. The main belt portion includes a back section, a left side section, a right side section, a left connective section between the back section and the left side section, and a right connective section between the back section and the right side section. The back section is wider than the other sections of the main belt portion. The main belt portion has a generally conical shape to be secured around a user's pelvic girdle and to align the respiratory component over the lumbar region of the user's spine to distribute a weight of the respiratory component. The belt buckle portion includes a right piece connected to the right side section of the main belt portion and a left piece connected to the left side section of the main belt portion.

40 Claims, 16 Drawing Sheets

U.S. PATENT DOCUMENTS

| | | | | |
|---|---|---|---|---|
| 6,206,257 | B1 | 3/2001 | Peele et al. | |
| 6,213,385 | B1 | 4/2001 | Stocke et al. | |
| 6,394,088 | B1 * | 5/2002 | Frye et al. | 128/204.26 |
| 6,575,165 | B1 | 6/2003 | Cook et al. | |
| 6,619,286 | B2 * | 9/2003 | Patel | 128/204.26 |
| 6,776,767 | B2 * | 8/2004 | Reinecke et al. | 602/19 |

* cited by examiner

ANATOMICALLY FITTED RESPIRATORY COMPONENT BELT

BACKGROUND OF THE INVENTION

The present invention relates to a respiratory protection system. In particular, the invention concerns a waist-mounted respiratory component system including a decontaminatible belt for supporting a respiratory component. The belt is ergonomically designed for improved comfort and support to a user.

Fan-forced positive pressure breathing apparatus, commonly known as Powered Air Purifying Respirators (PAPRs), and other respiratory components are used by first responders (HazMat, police, fire, and civil defense), military or other emergency response units to manage hazardous respiratory exposure. These respirators are also generally used in industrial applications, where the environmental hazards are well defined and quantified. Respiratory hazards might include harmful gases, vapors, and particulate matter. Respirators include a breathing mask, or other suitable hood, helmet or headtop, having a filtered air inlet. Respirators are employed to continually supply positive pressure to the wearer's mask. The filtered supplied air replenishes the internal confines of the mask and is continually ejected.

Respirators are currently typically attached to a belt threaded through slots in the back of the respiratory component, where the belt is formed from a relatively narrow strip (e.g., 2 inches) of stitched webbing. The responder wears the belt carrying the respirator around his or her waist and the load is normally attached to the rear of the belt. In addition to carrying the respirator, the responder also wears or carries additional equipment, such as a hood, protective clothing, and protective footwear, some of which may also be attached to the belt.

FIG. 1 is a side view of a user 10 and FIG. 2 is a schematic illustration of the user's lower spine and pelvis. A lower part of a user's back, a lumbar component 12 of a vertebral column 14 (i.e., spine), strengthens in response to weight bearing and works in concert with a pelvis 16, and in particular a hip 18, to carry the load of the upper body. When a load is carried by the user, such as on the shoulders, back, or hip, it is critical to carry the load in such a manner so as not to over stress the individual's back. This is especially important when loads of a repetitive nature, such as might be found in a workplace, are experienced.

The user, when postured in a relaxed upright stance, (shown in FIG. 1) as one might stand on a factory floor, causes the spine 14 and the hip 18 to orient in a definable way, defining a sacral angle 20. The sacral angle 20 is the inclined angle that occurs between an imaginary place 22 that horizontally transverses the hip 18 and a plane 24 aligned with the top of a sacrum 26, a lower portion of the spine 14. For weight bearing purposes, an optimum sacral angle 20 is one that minimizes stress on both the ligaments and the muscles of the lower back. From a biomechanical standpoint an optimum sacral angle 20 is generally considered to be about 30 degrees. A sacral angle 20 less than 30 degrees is caused when the pelvis 16 is rotated back (e.g., in direction of arrow 17); this orientation can place undue stress on the ligaments of the spine 14. In contrast, a sacral angle 20 greater than 30 degrees occurs when the pelvis 16 is rotated forward (e.g., in direction of arrow 19), creating a posture that stresses the muscularity of the back.

When a device is worn around a user's waist for the purposes of load carrying, it is important that the weight be properly displaced between the hip 18 and the spine 14 and that an optimum posture, as defined by the sacral angle 20, be promoted.

To provide a comfortable and supportive fit, the belt must be held tightly against the wearer's body. Wearing a typical webbing belt with an attached respiratory component around a wearer's waist does not position the respiratory component firmly and rigidly against the wearer's body. Improper positioning of the load of the respiratory component on a wearer's back does not provide efficient distribution and transfer of loads to the user's skeletal frame, and the user discomfort and fatigue results. With the respiratory component load placed to the rear of the belt, the front of the belt tugs in a rearward direction on the front of the belt creating an uncomfortable and unnecessary force on the lower abdominal muscles.

Belts formed from a strip of material are not easily adaptable to a variety of user body types, although the belt may be adaptable with regard to girth generally. Persons with exaggerated or minimal protrusions at the stomach or buttocks area require adjustable width and length of the belt to address the variances in their anatomy.

In use, the respiratory component is generally exposed to hazardous environments, which causes contamination to the belt. While some materials and surfaces are readily decontaminatible, others such as stitched fabric or webbing are difficult to decontaminate. Existing fabric belts and straps are difficult to effectively clean because debris and toxins may become trapped in the fabric and/or stitching so as to resist removal and require costly cleaning procedures. Discarding contaminated equipment is costly and not desirable. Therefore, responders desire a belt that can be decontaminatible after each use, so that it can be reused.

There exists a need for a waist-mounted respiratory protection system that is decontaminatible and provides improved comfort and stability. The belt should be relatively inexpensive and adaptable to a variety of wearers. The belt should facilitate easy decontamination of the respiratory protection system and an anatomically correct fit for a variety of user body types.

BRIEF SUMMARY OF THE INVENTION

The present invention is directed to a belt for use in carrying one or more waist-mounted respiratory protection components. The belt includes a main belt portion and a belt buckle portion. The main belt portion has a back section, a left side section, a right side section, a left connective section between the back section and the left side section, and a right connective section between the back section and the right side section. The back section is wider than the other sections of the main belt portion and has a plurality of slots therein for use in mounting a respiratory protection component thereon. The left and right side and connective sections are symmetrically shaped relative to the back section and each side section has a generally horizontal forward segment and a downwardly angled rearward segment.

The belt buckle portion includes a right piece connected to the right side section of the main belt portion and a left piece connected to the left side section of the main belt portion. At least one of the right and left pieces of the belt buckle portion is adjustable in length, and free ends of the right and left pieces are selectively connected together by a releasable buckle.

The main belt portion is shaped to be secured around a user's pelvic girdle and to align the respiratory component thereon over the lumbar region of the user's spine, at an ideal angle of inclination of approximately 15 degrees, to distribute a weight of the respiratory component around a pelvis of the user, allow free leg movement, minimize pinching adjacent a user's iliac crests during such movement, and shift the rotational momentum of the weight of the respiratory component toward the user, thus further enhancing user comfort.

BRIEF DESCRIPTION OF THE DRAWINGS

The present invention will be further explained with reference to the attached figures, wherein like structure is referred to by like numerals throughout the several views.

While the above-identified drawing figures set forth several embodiments of the invention, other embodiments are also contemplated, as noted in the discussion. In all cases, this disclosure presents the present invention by way of representation and not limitation. It should be understood that numerous other modifications and embodiments can be devised by those skilled in the art which fall within the scope and spirit of the principles of this invention.

DETAILED DESCRIPTION

Figure 3:
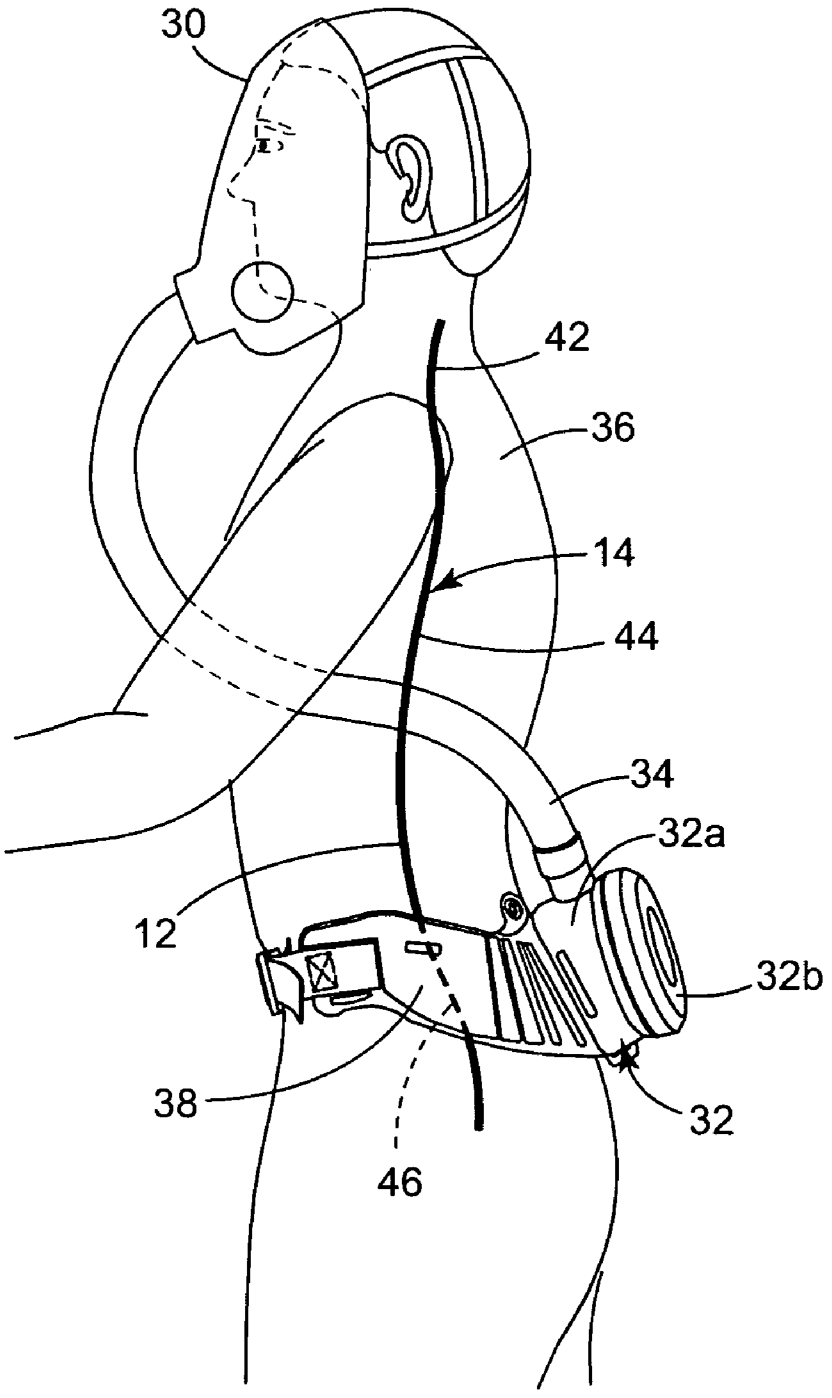
FIG. 3 is perspective and diagrammatic view of a respiratory protection system worn by a user.

A respiratory protection system worn by a user is shown in FIG. 3. The respiratory protection system includes a breathing face-piece 30, or head gear, and a respiratory component 32, such as a fan-forced positive pressure breathing device, commonly known as a Powered Air Purifying Respirator (PAPR), an air filter or monitor. An air hose 34, or tube, connects the respiratory component 32 to the breathing face-piece 30 to supply breathable air to a user 36. The respiratory component 32 is designed to be worn by a person working in an atmosphere with unwanted contaminants, including respiratory hazards. The PAPR 32 has a housing 32*a* and one or more filter units 32*b*, which serve to filter unwanted contaminants from the surrounding atmosphere, thus allowing a user wearing the PAPR to work in contaminated or hazardous areas. The PAPR 32 typically has a weight in the range of about 0.3 Kg to about 3.0 Kg. One example of a PAPR is disclosed and described in U.S. Pat. No. 6,575,165, entitled "Apparatus and Method for Breathing Apparatus Component Coupling," which has a weight of about 1.4 Kg.

The present invention concerns an anatomically fitted, ergonomically designed belt 38 for carrying the respiratory component 32. The belt 38 may also be used with a variety of respiratory components for hands-free use in contaminated areas. The respiratory component 32 is attached to the anatomically fitted belt 38 for carrying by the user and positioned such that the load is carried at the rear of the belt 38.

Figure 1:
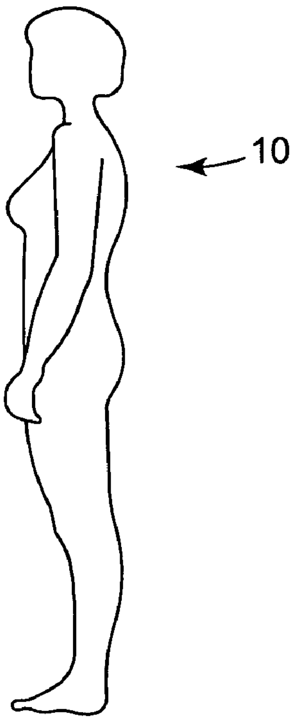
FIG. 1 is a side view of a person.

The respiratory component 32 attached to the belt 38 allows carriage by the user 36 leaving the hands free for other purposes. In addition, the belt 38 is configured to provide an anatomical fit wherein the hips carry the load of the respiratory component 32, leg movement is freed, and the lumbar of the back is firmly supported. The belt 38 also cushions the back of the user 36 while still maintaining rigidity to support the respiratory component 32. In FIG. 1, line 14 represents the curvature of a user's spine, including an upper cervical region 42, a kyphotic curve 44, lower lumbar region 12 and a lordotic curve 46. The respiratory component 32 and the belt 38 is formed from a decontaminatible material such that after use in hazardous areas, the belt 38 may be decontaminated for future reuse.

Loads on the spine are produced primarily by body weight, muscle activity, prestress exerted by the ligaments, and externally applied loads. The lumbar region 12 is the main load-bearing area of the spine 14. The spine 14 can be considered as a modified elastic rod because of the flexibility of the spinal column, the shock-absorbing behavior of the discs and vertebrae, the stabilizing function of the longitudinal ligaments, and the elasticity of the ligamenta flava. The two curvatures of the spine in the sagittal plane, kyphotic 44 and lordotic 46, also contribute to the spring like capacity of the spine and allow the vertebral column to withstand higher loads than if it were straight. The extrinsic support provided by the trunk muscles helps stabilize and modify the loads on the spine 14 in both dynamic and static situations.

When a persons stands, the postural muscles are constantly active. This activity is minimized when the body segments are well aligned. During standing, the line of gravity of the trunk usually passes ventral to the center of the fourth lumbar vertebral body. Thus, it falls ventral to the transverse axis of motion of the spine 14 and the motion segments are subjected to a forward-bending moment, which must be counterbalanced by ligament forces and erector spinea muscle forces. Any displacement of the line of gravity alters the magnitude and direction of the moment of the spine 14. For the body to return to equilibrium, the moment must be counteracted by increased muscle activity, which causes intermittent postural sway.

The pelvis 16 also plays a role in the muscle activity and resulting loads on the spine 14 during standing. The base of the sacrum 26 is inclined forward and downward. The angle of the inclination, or sacral angle 20, is about 30 degrees to the transverse plane during relaxed standing. Tilting of the pelvis 16 about the transverse axis between the hip joints changes the angle. When the pelvis 16 is tilted backward, the sacral angle 20 decreases and the lumbar lordosis flattens. This flattening affects the thoracic spine, which extends slightly to adjust the center of gravity of the trunk so that energy expenditure, in terms of muscle work, is minimized. When the pelvis 16 is tilted forward the sacral angle 20 increases, accentuating the lumbar lordosis and the thoracic kyphosis. Forward and backward tilting of the pelvis 16 influences the activity of the postural muscles by affecting the static loads on the spine 16.

Body position affects the magnitude of the loads on the spine 14. These loads are minimal during well supported reclining and remain low during relaxed up-right standing. The present invention belt displaces the load of the respiratory component between the spine 14 and the pelvis 16 such that an optimum posture defined by the sacral angle 20 occurs.

Figure 4:
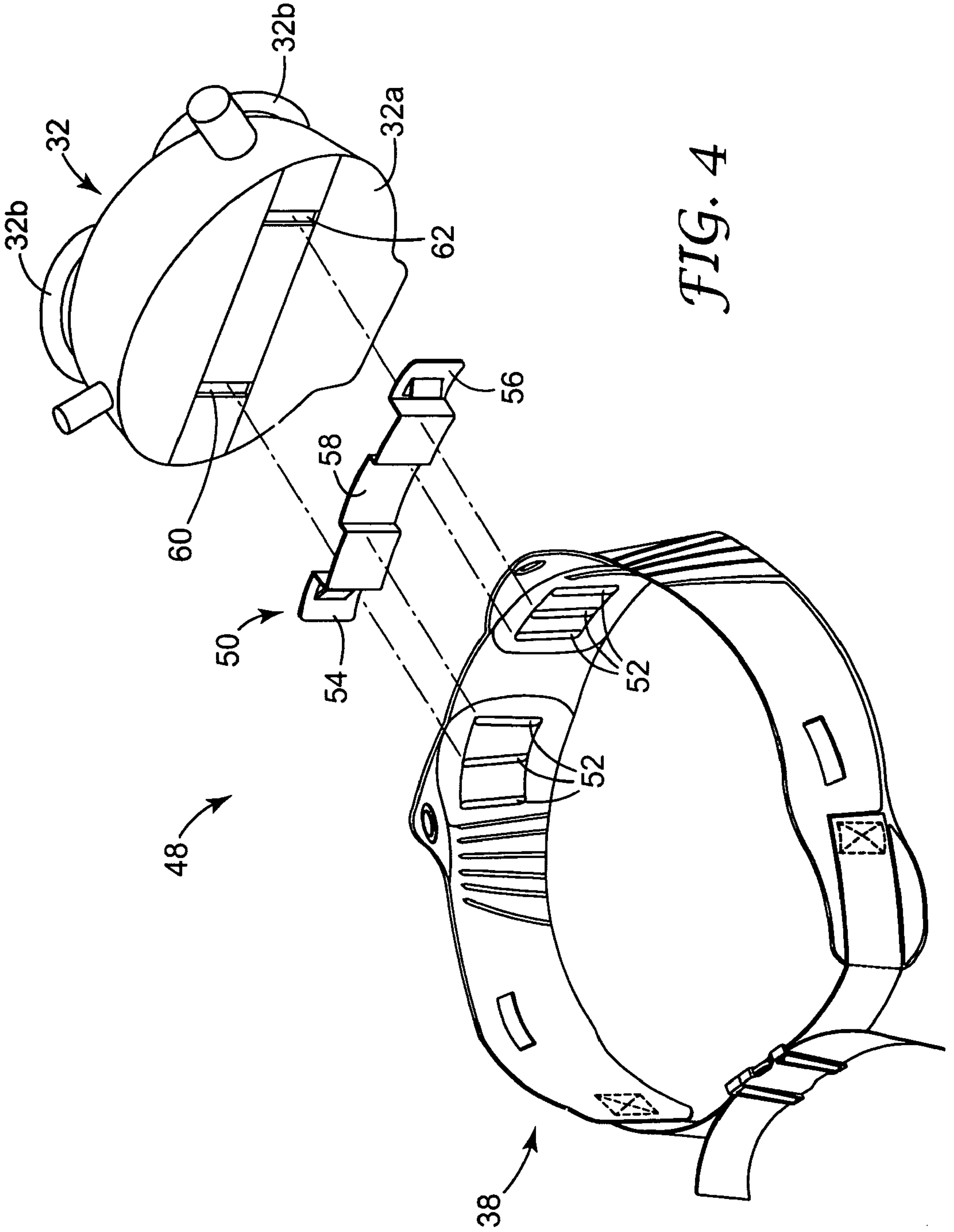
FIG. 4 is an exploded perspective view of a waist-mounted respiratory component system.
Figure 18:
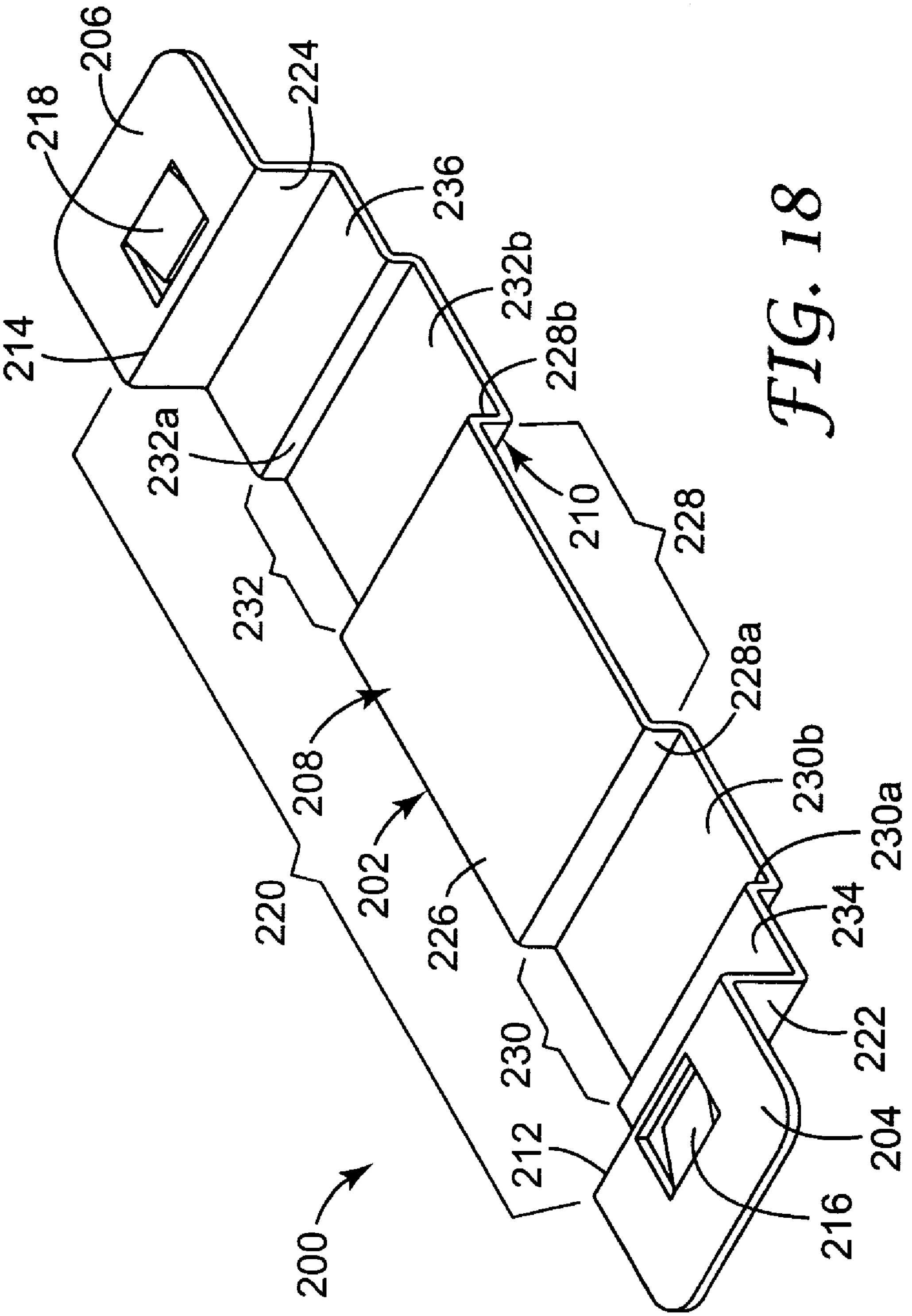
FIG. 18 is a perspective view of a further embodiment of a respiratory component mounting clip.

FIG. 4 is an exploded perspective view of a waist-mounted respiratory component system 48. The waist-mounted respiratory component system 48 includes the belt 38, a mounting assembly 50 (discussed in detail below with respect to FIGS. 13-16 and 18-19) for mounting the respiratory component 32 to the belt 38, and the respiratory component 32. In one embodiment, the belt 38 includes a plurality of spaced apart mounting slots 52, or clip openings, for attaching the mounting assembly 50 to the belt 38. The mounting assembly 50 is a clip that is woven through the slots 52 of the belt 38 such that first and second ends 54, 56 of the mounting assembly 50 are free for attaching to the respiratory component 32 and an intermediate portion 58 is connected to the belt 38 (as shown in FIGS. 14, 16 and 18). In further embodiments of the respiratory component system 48, the belt 38 and the mounting assembly 50 are a unitary component. For example, the belt 38 may include tabs, or projections, permanently attached thereto for mounting the respiratory component 32 thereon. U.S. patent application Ser. No. 10/749,177 entitled "Respiratory Component Mounting Assembly" and filed on the same date herewith, discusses the mounting assembly 50 in further detail and is incorporated herein by reference. The respiratory component 32 includes at least two spaced apart openings 60, 62 for receiving the free ends 54, 56 of the mounting clip 50. Although the mounting slots 52 and clip openings 60, 62 shown in FIG. 4 are generally parallel and vertically aligned, those skilled in the art will recognize that other configurations and orientations for the slots and openings are possible.

Figure 5:
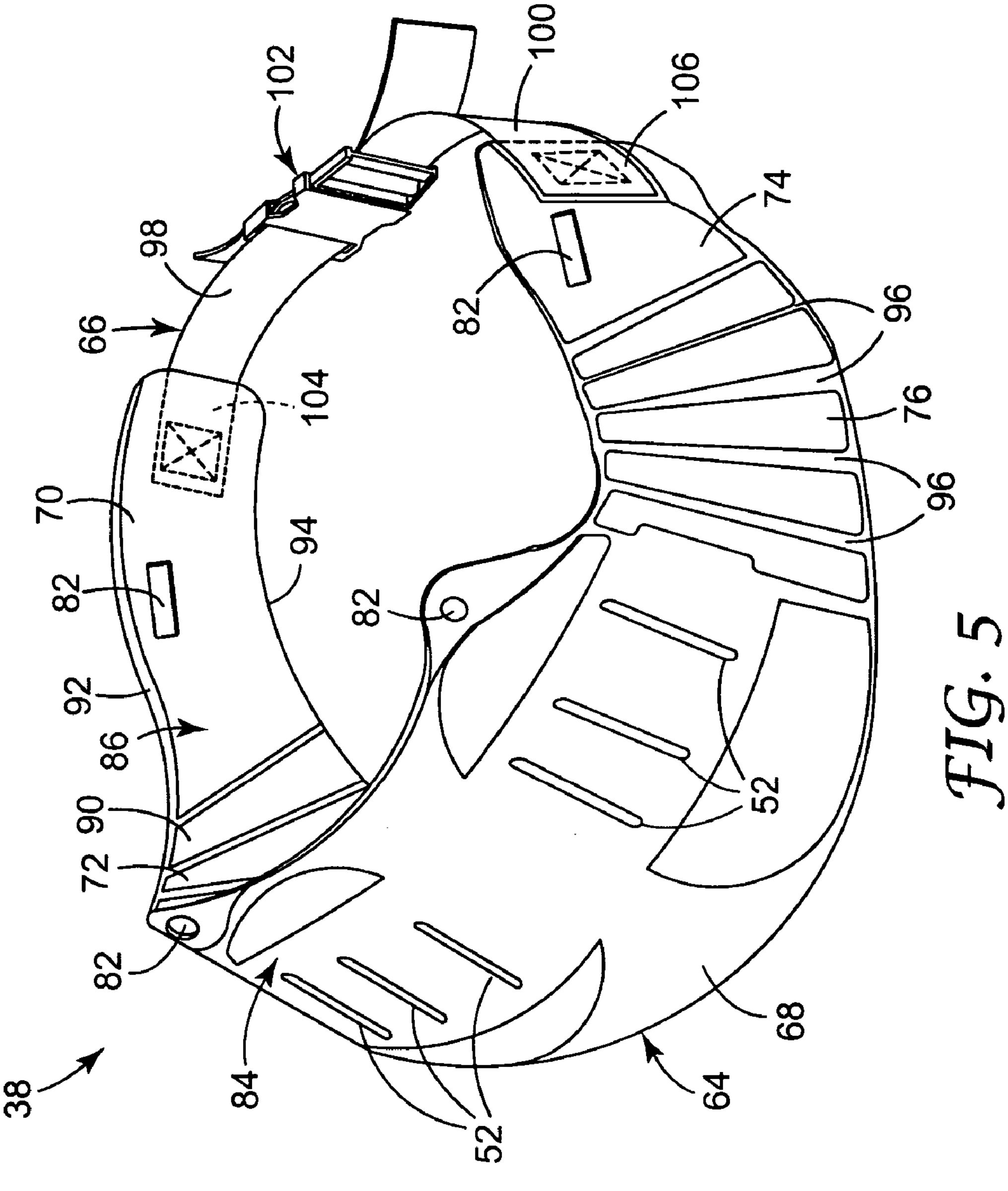
FIG. 5 is a perspective view of a belt for carrying one or more waist-mounted respiratory protection components.
Figure 6:
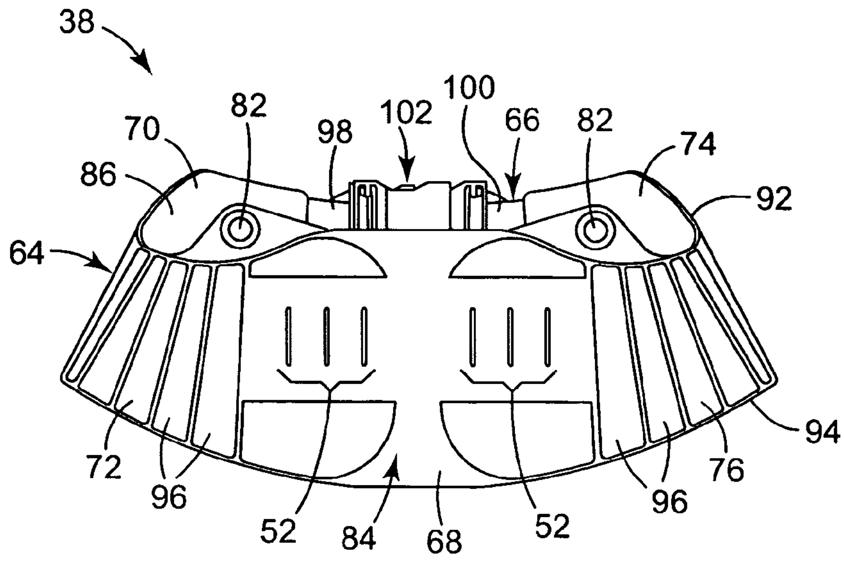
FIG. 6 is a back (outer) perspective view of the belt of the waist-mounted respiratory component system.
Figure 7:
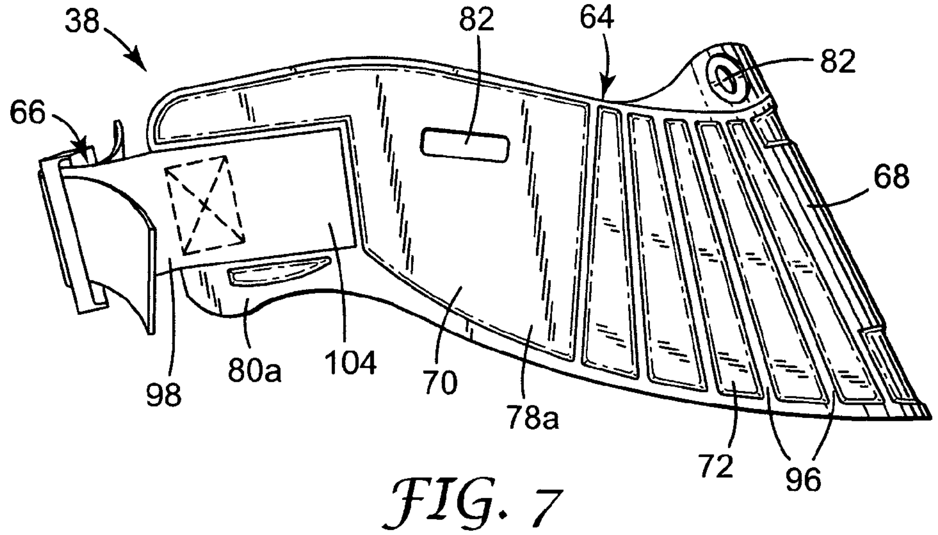
FIG. 7 is a side view of the belt of the waist-mounted respiratory component system.
Figure 8:
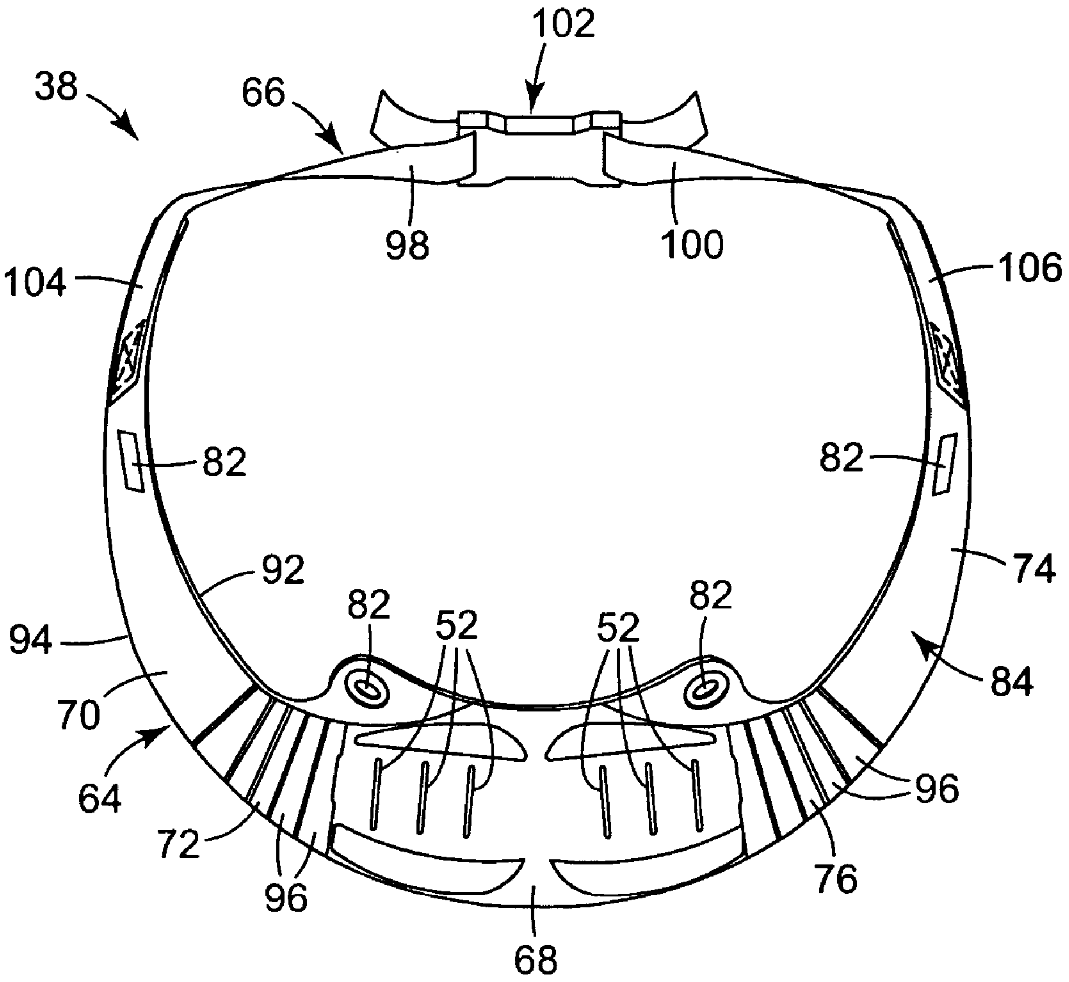
FIG. 8 is a top perspective view of the belt of the waist-mounted respiratory component system.
Figure 9:
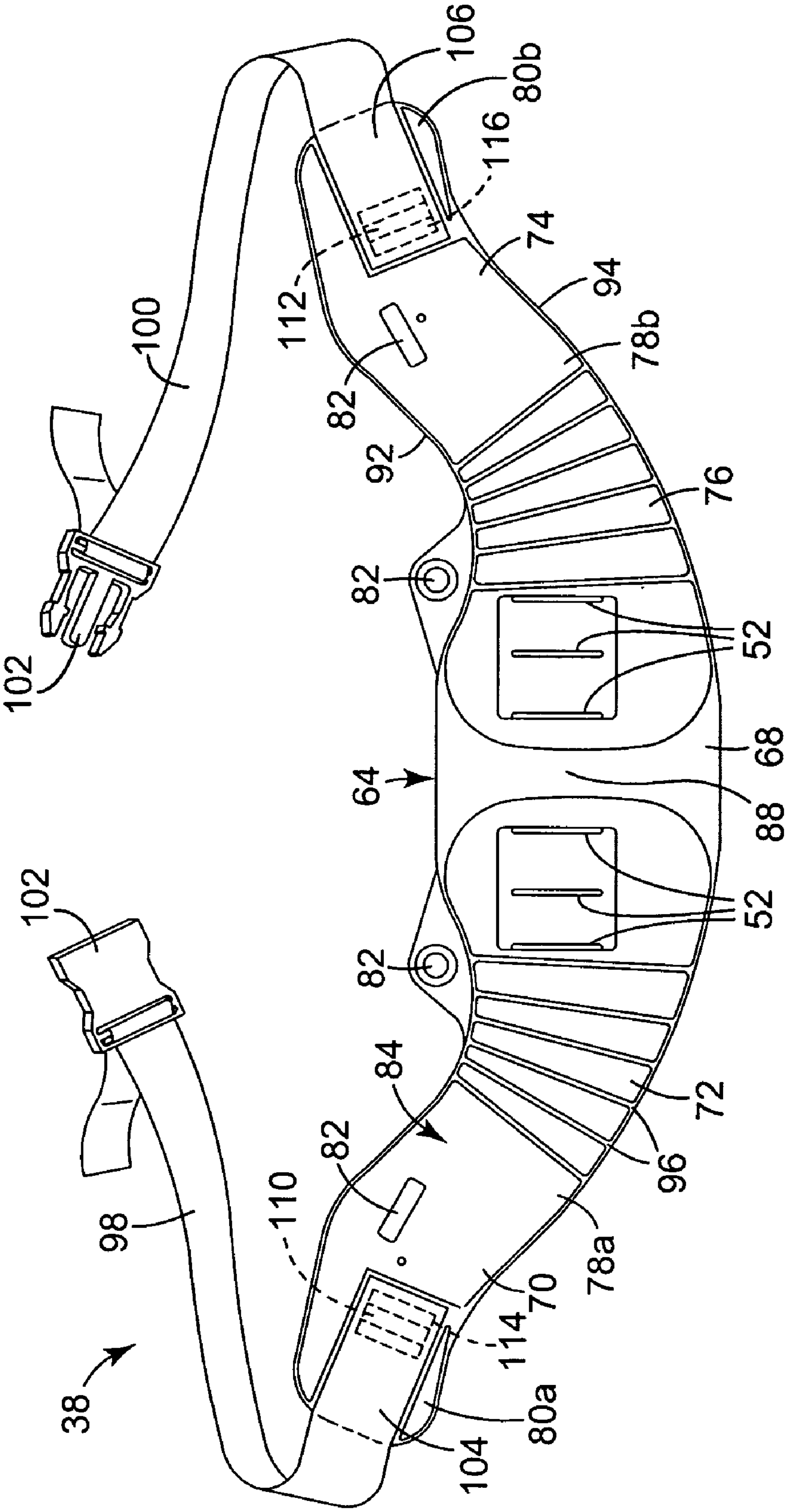
FIGS. 9 and 10 are views of the interior of the belt of the waist-mounted respiratory component system.
Figure 10:
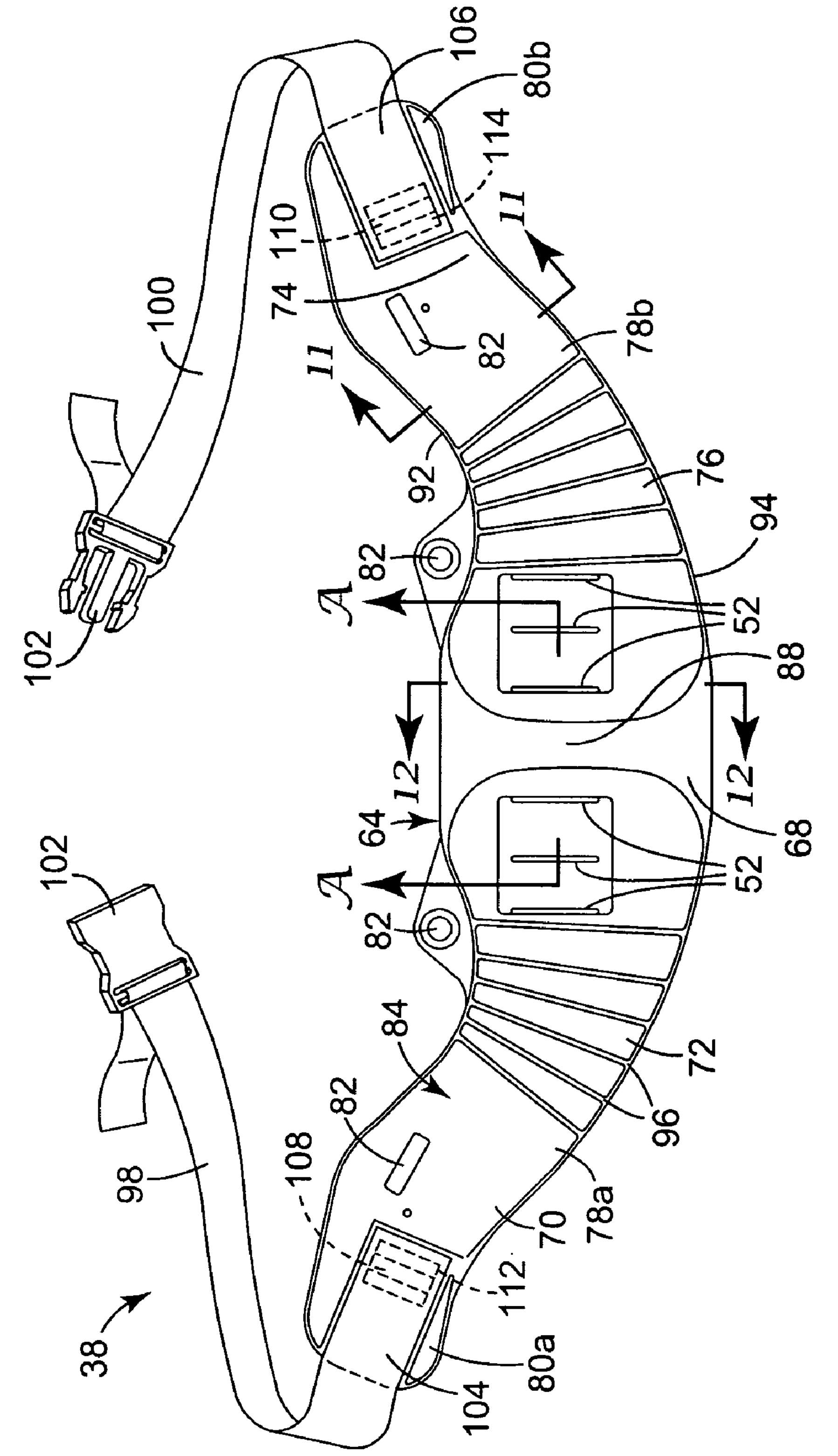
Figure 11:
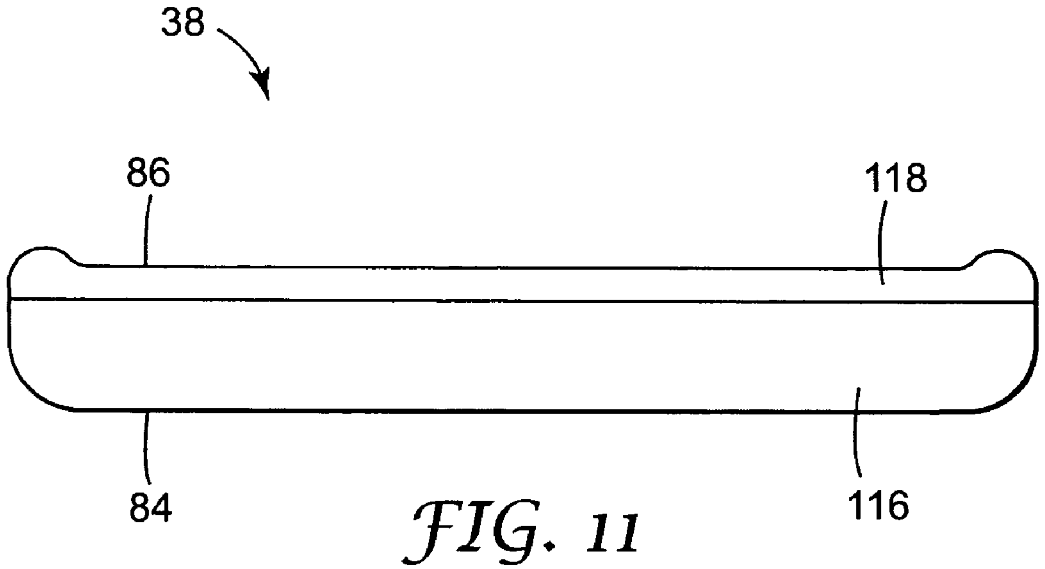
FIG. 11 is a cross-sectional view of the belt taken along line 11-11 of FIG. 10.
Figure 12:
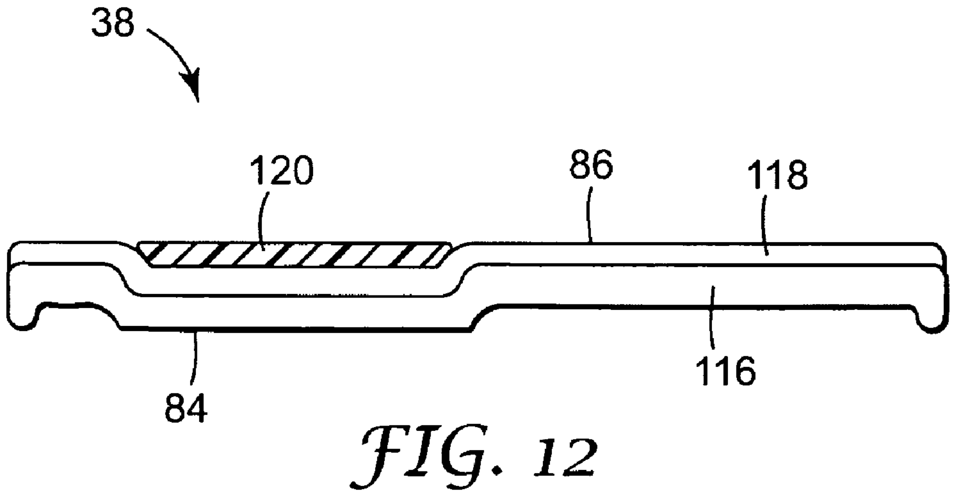
FIG. 12 is a cross-sectional view of the belt taken along line 12-12 of FIG. 10.

FIGS. 5-12 show an embodiment of the respiratory protection system belt 38. FIG. 5 provides a perspective view of the belt 38, while FIGS. 6, 7, and 8 provide back (outer), side and top views, respectively. FIGS. 9 and 10 are inner views of the belt 38 and FIGS. 11 and 12 are cross-sectional views of the belt 38 taken along lines 11-11 and 12-12, respectively, of FIG. 10.

The belt 38 for carrying one or more respiratory components 32 includes a main belt portion 64 and a belt buckle portion 66 connected to the main belt portion 64. The main belt portion 64 includes a back section 68, a left side section 70, a left connective section 72 between the back section 68 and the left side section 70, a right side section 74 and a right connective section 76 between the back section 68 and the right side section 74. The left and right side sections 70, 74 and the left and right connective sections 72, 76 are symmetrically shaped relative to the back section 68. Each side section 70, 74 has a generally horizontal forward segment **78*a* and 78*b* and a downwardly angled rearward segment 80*a* and 80*b* (shown in FIG. 7**).

The back section 68 is wider than the other sections of the main belt portion 64 to provide support for the respiratory component 32 and distribute the load of the respiratory component to a user's hips. The back section 68 includes two sets of mounting slots, each comprised of three slots 52. Those skilled in the art will recognize that further embodiments of the belt 38 include fewer or more mounting slot sets comprised of fewer or more slots 52. The slots 52 are used for mounting the respiratory component 32 to the belt 38, and in particular, receive the mounting assembly 50. The main belt portion 64 may include connector elements 82 for use in mounting additional supportive or respiratory components to the belt 38.

The main belt portion 64 includes an outer face 84 and an inner face 86. As seen in FIG. 10, at the back section 68 of the main belt portion 64, the inner face 86 has a generally vertically disposed recess 88 therein, which serves as an air flow channel. The recess 88 channels air along the belt 38, thereby making the belt 38 cooler to wear and reducing user perspiration. In addition, the inner face 86 at the connective sections 72, 76 includes generally vertically disposed channels 90 (FIG. 5). The channels 90 direct air away from a user's body, which gives breathability to the belt 38.

Figure 2:
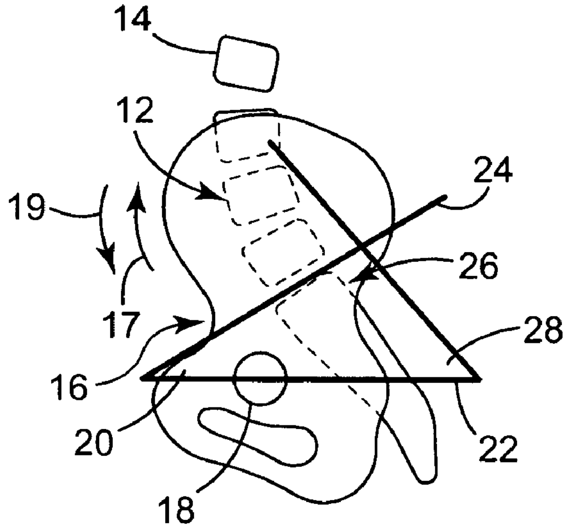
FIG. 2 is a schematic illustration of a person's lower spine and pelvis.

The main belt portion 64 has a substantially conical shape such that the belt 38 secures around a user's pelvic girdle and aligns the respiratory component 32 thereon over the lumbar region 12 of a user's spine 14. The main belt portion 64 is aligned over the lumbar region at an angle of inclination 28 of about 15 degrees (i.e., −75 degrees from the hip plane 22 shown in FIG. 2). The belt 38 distributes the weight of the respiratory component 32 around a user's pelvis 16 such that a user's hips carry the load of the respiratory component 32. In addition, the shape and the position of the main belt portion 64 allows free leg movement of the user 36 and minimizes pinching adjacent a user's iliac crests during such movement. The position of the main belt portion 64 with respect to a user's spine 14 shifts the rotational momentum of the weight of the respirator component 32 to the user 36. Overall, the shape of the main belt portion 64 of the belt 38 facilitates positioning of the respiratory component 32, while the belt 38 is worn by a user, over a user's lumbar region 12 at an angle of inclination 28 to enhance comfort of a user.

The main belt portion 64 has an upper peripheral edge 92 and a lower peripheral edge 94. As shown in FIGS. 5-8, the main belt portion 64 includes a flared portion at which the lower edge 94 extends outwardly, relative to a user, beyond the upper edge 92. Thereby, a diameter of the belt 38 along the upper peripheral edge 92 is less than a diameter of the belt 38 along the lower peripheral edge 94. Although the flared portion shown in the present embodiment extends along the entire main belt portion 64, including the left and right side sections 70, 74, in further embodiments of the belt 38 the flared portion is defined by the back section 68 only or a combination of the back section 68 and connective sections 72, 76. Each connective section 72, 76 of the main belt portion 64 includes hinges 96 that radiate downwardly and outwardly from the upper edge 92. The hinges 96 facilitate bending in use to accommodate movement of the user 36.

The belt buckle portion 66 of the belt 38 includes a left piece 98 connected to the left side section 70 of the main belt portion 64 and a right piece 100 connected to the right side section 74 of the main belt portion 64. Each piece 98, 100 of the belt buckle portion 66 is adjustable in length, although in further embodiments of the belt only one piece may be adjustable. Free ends of the left and right pieces 98, 100 are selectively connected together by a buckle 102, such as a releasable buckle, or any other buckle known in the art.

As shown in FIGS. 5-8, first ends 104, 106 of the left and right pieces 98, 100 of the belt buckle portion 66 connect to the respective left and right side sections 70, 74, for example, by stitching or adhesive. In further embodiments of the belt 38 (as shown in FIGS. 9 and 10), the left and right pieces 98, 100 are releasably connected to the side sections 70, 74 to accommodate separation of the belt buckle portion 66 from the main belt portion 64. A releasable belt buckle portion 66 is desired when the left and right pieces 98, 100 are not comprised of a decontaminatible material. Thus, the left and right pieces 98, 100 are detachable for disposal and the main belt portion 64 may be decontaminated for reuse. Each side section 98, 100 includes an opening 108 and 110 for receiving the first end 104, 106 of the respective belt piece 98, 100 and the first end 104, 106 of each belt piece 98, 100 includes a hinged connective member 112 and 114. To attach or release the belt piece 98, 100 from the main belt portion 64, the connective member 112, 114 folds at its hinge to narrow the connective member 112, 114 to facilitate sliding of the connective member 112, 114 through the opening 108, 110 of the side section 70, 74. In an attached position, the connective member 112, 114 is unfolded at the hinge such that the connective member 112, 114 is wider than the opening 108, 110 to prevent removal of the belt piece 98, 100 from the main belt portion 64. In further embodiments of the belt 38, other suitable connection mechanisms are possible, such as snap-fit, interlocking members, or the like.

As shown in FIGS. 11 and 12, in the one embodiment, the main belt portion 64 is formed as a laminate having an outer layer 116 and an inner layer 118. The outer layer 116 provides rigidity and the inner layer 118, which contacts a user's body, provides a cushioning layer. The main belt portion 64, and in particular the outer layer 116, is formed from a generally rigid material relative to the left and right pieces 98, 100 of the belt buckle portion 66. The main belt portion 64 is generally more rigid than the belt buckle portion 66, which facilitates support of the respiratory component 32 and distributes the weight of the respiratory component 32 across the main belt portion 64. In addition, the slots 52 in the back section 68 of the main belt portion 64 are reinforced with a reinforcement member 120, such as a plate. While two plates or members 120 are shown, one may suffice, or there may be more than two (e.g., one plate for each mounting slot 52). The reinforcement member 120 stabilizes the respiratory component 32 and prevents separation of the respiratory component 32 and the mounting assembly 50 or the belt 38, and movement of the respiratory component away from the belt 38.

The respiratory protection system is generally used in hazardous and contaminated environments, thereby requiring that the belt 38, and other components (e.g., respiratory component 32 and mounting assembly 50) be readily decontaminatable such that it maybe reused in further applications. In one embodiment, both the outer layer 116 and the inner layer 118 of the main belt portion 64 are formed from an ethyl vinyl acetate (EVA) co-polymer with a polyolefin elastomer. One suitable EVA is made by Alveo (a Sekisui Company of Luzem, Switzerland). In one embodiment, the outer layer 116 EVA has a density of about 125 kg/m$^3$ and the inner layer 118 EVA has a density of about 70 kg/m$^3$ to about 75 kg/m$^3$. Thereby the outer layer 116 is more rigid than the inner layer 118 to provide rigidity and structure, whereas the inner layer 118 is less rigid and serves as a cushioning inner layer of the main belt portion 64 to provide more comfort to a user. In one embodiment, the outer layer 116 has a thickness of about 3 mm (in non-embossed areas) and the inner layer 118 has a thickness of about 5 mm. EVA is a decontaminatable material and abrasion resistant, whereby if the main belt portion 64 is damaged (i.e., nicked), it will remain decontaminatable. In further embodiments of the main belt portion 64, the outer layer 116 is formed from a rigid, high density polyethylene (HDPE). In one embodiment, the reinforcement members 120 of the slots 52 are formed from a low density polyethylene, such as an LDPE made by VTS Plastics (Liverpool, UK), having a thickness of about 1.5 mm. The belt 38 typically has a weight of about 240 grams. In further embodiments of the belt 38, the main belt portion 64 is formed from a single, solid layer EVA or a foam surrounded by a polyurethane coated fabric. Whatever material is used to form the main belt portion should be a material that does not readily carry debris or contaminates, or bear a coating thereon having such contaminant resistant characteristics.

To form the main belt portion 64 of the belt 38, sheets of EVA material for the outer and inner layers 116, 118 are flame laminated together. Each layer of material is heated until there is a thin layer of molten material on its surface. The two layers are than pressed together (e.g., embossing) and the materials weld together as each layer cools. The belt shape, slots, channels, hinges and other openings are formed in the main belt portion, for example, by stamping and/or embossing. In one embodiment, optional reinforcement members are attached to the main belt portion by an EVA hot melt adhesive. In further embodiments of the belt, the outer layer and inner layer are joined together with a suitable adhesive, such as an epoxy resin or a double-sided adhesive tape, or additional attachment means are used to attach the reinforcement members to the belt, such as stitching, welding or suitable fasteners.

In one embodiment, the belt buckle portion 66 is formed from readily decontaminatible material. The belt pieces 98, 100 are formed from a polyester coated with polyurethane or PVC, which allows the belt buckle portion 66 to be wiped clean of contaminants. In embodiments where the belt buckle portion 66 includes thread, the thread areas may collect contaminates and are generally decontaminatible. Releasably connecting the belt buckle portion 66 to the main belt portion 64 permits the contaminated pieces to be removed, disposed and replaced with new, clean pieces, thereby maintaining the contamination-free nature of the entire belt.

Figure 13:
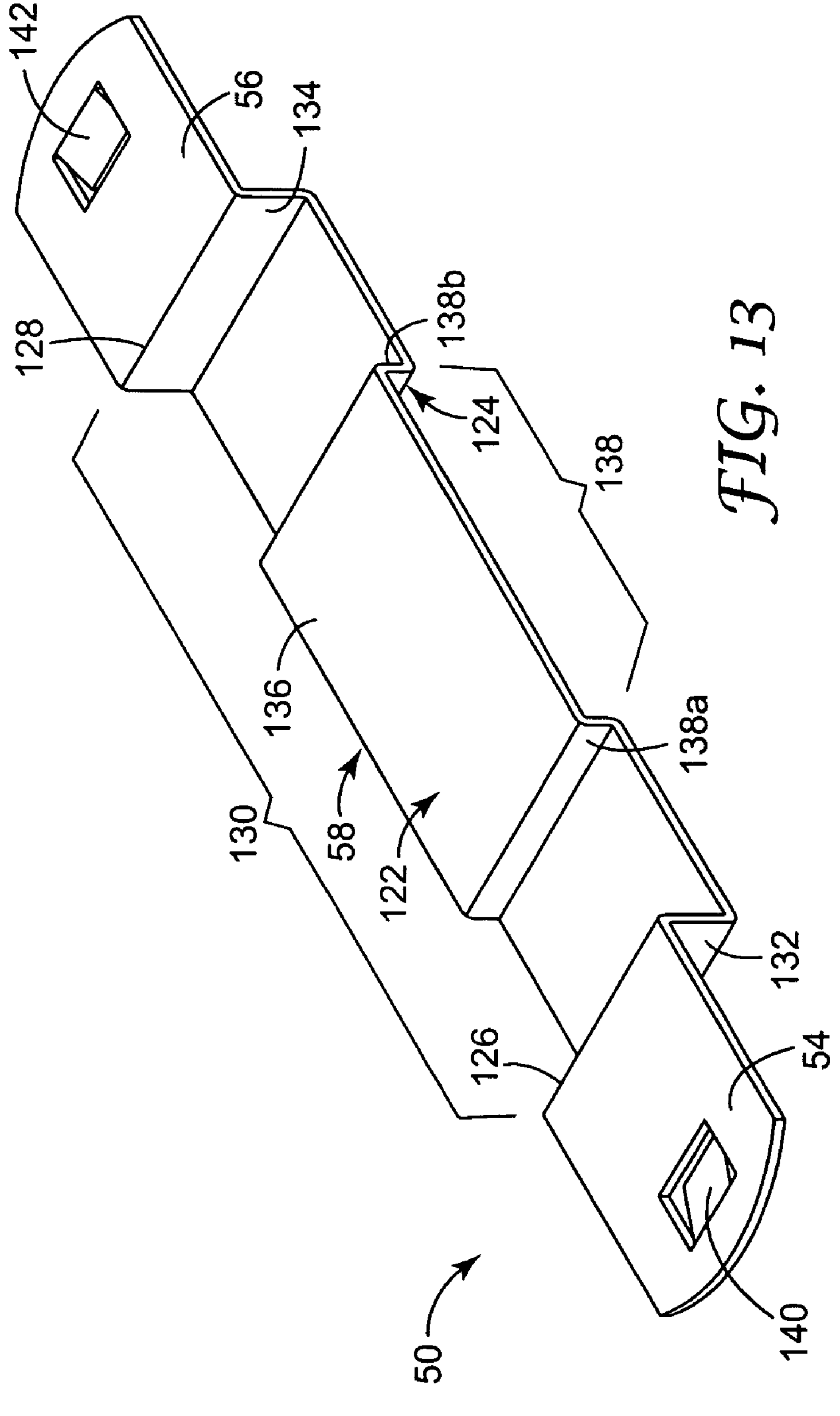
FIG. 13 is a perspective view of a respiratory component mounting clip.
Figure 14:
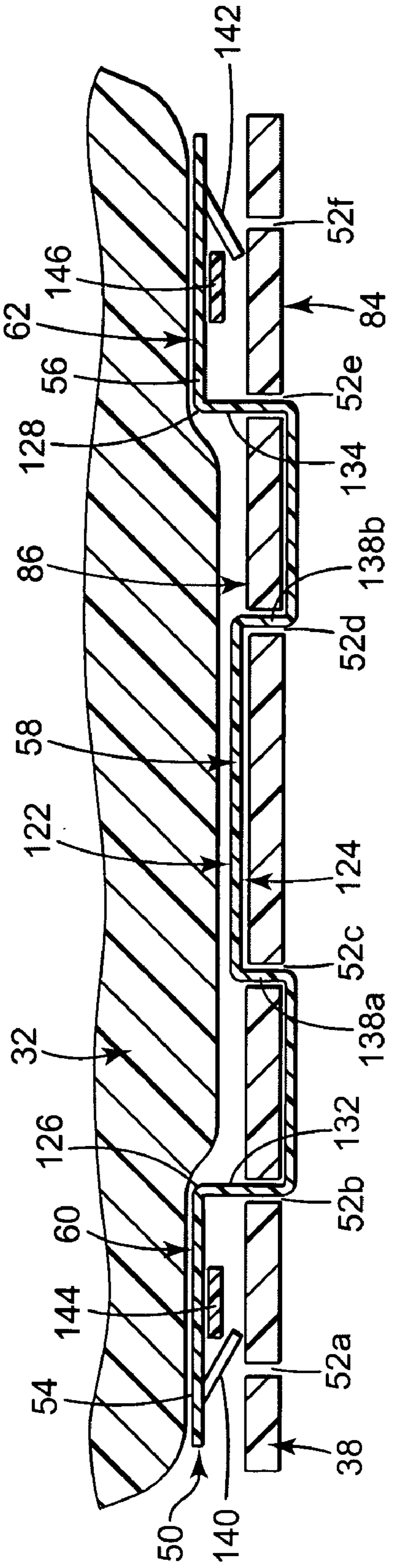
FIG. 14 is a schematic cross-sectional view of the waist-mounted respiratory component system, taken along line A-A of FIG. 10, and including the respiratory component mounting clip of FIG. 13.

FIG. 13 is a perspective view of mounting clip 50 for attaching the respiratory component 32 to the belt 38 and FIG. 14 is a cross-sectional view of the waist-mounted respiratory component system 48, taken along line A-A of FIG. 10, showing the respiratory component mounting clip 50 and the respiratory component 32 mounted to the inventive belt 38. The mounting clip 50 includes the intermediate portion 58, two spaced apart free ends 54, 56 connected to the intermediate portion 58, a first surface 122 and a second surface 124. The intermediate portion 58 extends between a first shoulder 126 and a second shoulder 128, while the first and second free ends 54, 56 extend from the first and second shoulders 126, 128, respectively. The free ends 54, 56 are aligned to extend in generally opposite directions.

The first surface 122 of the intermediate portion 58 defines a channel 130 extending between a first outer wall 132 and a second outer wall 134. The channel 130 includes a stepped portion 136 extending towards the first surface 122 and defining a second channel 138 on the second surface 124 of the mounting clip 50. A depth of the first channel 130 (defined by walls 132 and 134) is greater than a depth of the second channel 138 (defined by walls 138*a* and 138*b*). The first and second free ends 54, 56 of the mounting clip 50 include first and second biased detent tabs 140, 142 extending generally downwardly and inwardly from the second surface 124 of the mounting clip 50.

The mounting clip 50 is generally used to attach the respiratory component 32 to the belt 38. The intermediate portion 58 of the clip 50 is woven through the mounting slots 52*b*, 52*c*, 52*d*, and 52*e* of the belt 38, whereby the free ends 54, 56 project from the inner surface 86 of the belt 38. In the embodiment shown in FIG. 14, four of the mounting slots 52*b*, 52*c*, 52*d*, and 52*e* receive the intermediate portion 58 of the clip 50, and in particular walls 132, 138*a*, 138*b*, and 134, respectively. Between each adjacent mounting slot 52*b*, 52*c*, 52*d*, and 52*e*, one of the two surfaces 122, 124 of the clip 50 aligns against either the outer face 84 or the inner face 86 of the belt 38.

An example of a suitable respiratory component for use with the mounting clip 50 is JUPITER brand turbo unit (Part No. 085-00-05P) from 3M United Kingdom PLC (Bracknell, UK). The respiratory component 32 includes first and second openings 60, 62 for removably receiving the free ends 54, 56 of the clip 50. The respiratory component 32 also includes first and second opposed detent surfaces 144, 146 adjacent the first and second clip openings 60, 62, respectively. The openings 60, 62 of the respiratory component 32 receive the free ends 54, 56 of the clip 50 whereby the detent tabs 140, 142 of the clip 50 form a locking engagement with the detent surfaces 144, 146 of the respiratory component 32.

The mounting clip 50 firmly secures the respiratory component 32 to the belt 38 and prevents the respiratory component 32 from falling off the belt 38 during normal use, and provides strong enough attachment to prevent separation of the respiratory component 32 from the belt 38 even if caught on machinery or other apparatus. The mounting clip 50 provides easy attachment and detachment of the respiratory component 32 to and from the belt 38 and facilitates efficient interchange between respiratory components carried by the belt 38. To attach or remove the respiratory component 32 from the belt 38, the free ends 54, 56 of the clip 50 are inserted into or removed from the clip openings 60, 62 in the respiratory component 32. Detent tabs 140, 142 are pressed towards the second surface 124 of the clip 50 to facilitate insertion and removal of the clip from the respiratory component. At least the free ends 54, 56 of the clip 50 are flexibly resilient to accommodate insertion and removal to and from the clip openings 60, 62 of the respiratory component 32. The intermediate portion 58 of the clip 50 is sufficiently flexible to weave through the mounting slots 52 of the belt 38.

Figure 15:
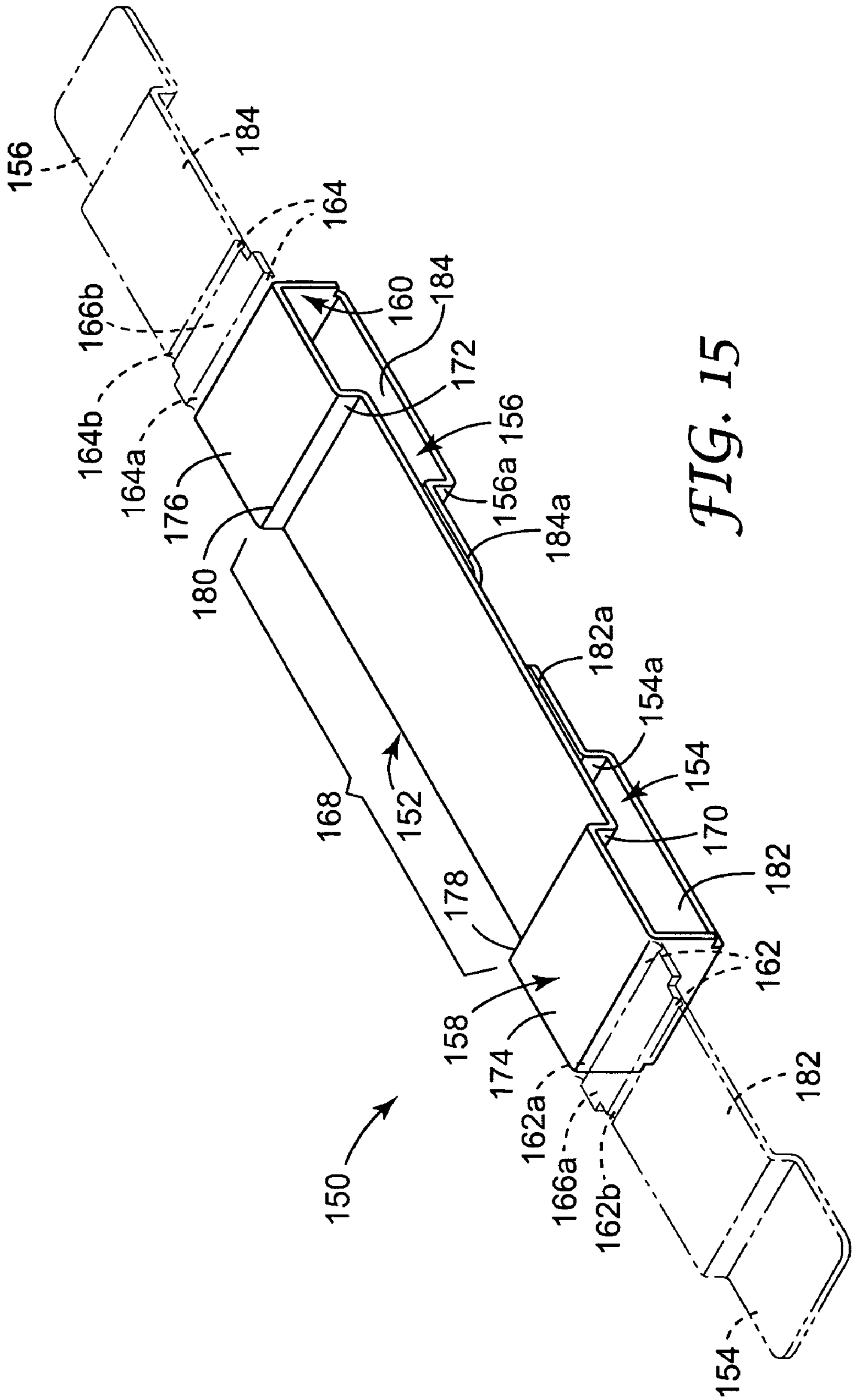
FIG. 15 is a perspective view of a further embodiment of a respiratory component mounting clip.
Figure 16:
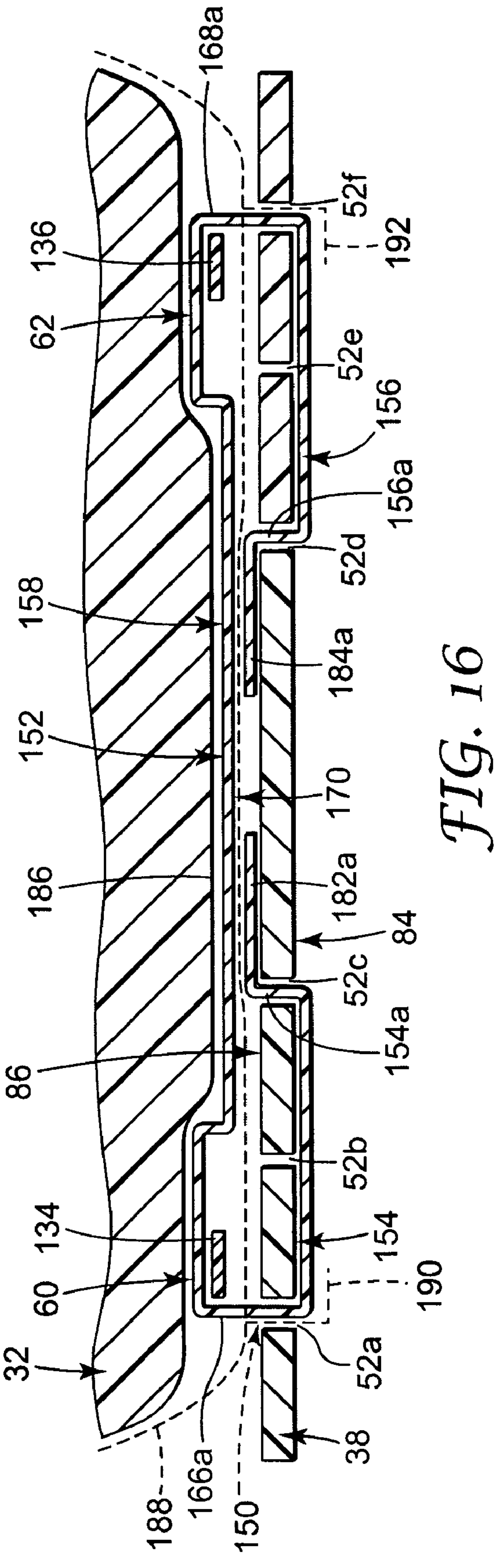
FIG. 16 is a schematic cross-sectional view of the waist-mounted respiratory component system, taken along line A-A of FIG. 10, and including the respiratory component mounting clip of FIG. 15.

FIG. 15 is a perspective view of a further embodiment of a mounting clip 150 for attaching the respiratory component 32 to the belt 38 and FIG. 16 is a cross-sectional view of the waist-mounted respiratory component system 48, taken along line A-A of FIG. 10, showing the respiratory component mounting clip 150 and the respiratory component 32 mounted to the inventive belt 38. The mounting clip 150 includes an intermediate portion 152, two spaced apart first and second free ends 154, 156 connected to the intermediate portion 152, a first surface 158 and a second surface 160. The intermediate portion 152 extends between a first pair of living hinges 162 and a second pair of living hinges 164, which connect the intermediate portion 152 to the first and second free ends 154, 156, respectively.

The free ends 154, 156 of the mounting clip 150 fold and extend, at the living hinges 162, 164, between a folded, use position (shown in solid lines in FIG. 15) and an extended position (shown in broken lines in FIG. 15). In the use position, the free ends 154, 156 are aligned to extend toward each other and the second surface 130 of the intermediate portion 152 and the free ends 154, 156 are generally horizontally aligned. Each pair of living hinges 162, 164 includes an upper hinge 162*a*, 164*a* and a lower hinge 162*b*, 164*b* spaced apart and separated by a connector wall 166*a*, 166*b*.

The first surface 158 of the intermediate portion 152 defines a channel 168 extending between a first channel wall 170 and a second channel wall 172. The intermediate portion 152 also includes first and second intermediate ledges 174, 176. The first intermediate ledge 174 extends from a first shoulder 178 adjacent the first channel wall 170 to the first, upper living hinge 162*a*. The second intermediate ledge 176 extends from a second shoulder 180 adjacent the second channel wall 172 to the second, upper living hinge 162*a*. Each free end 154, 156 is stepped, as at stepped walls 154*a* and 156*a*, and includes an end ledge 182, 184 generally parallel and horizontally aligned with its respective intermediate ledge 174, 176, when the free ends 154, 156 are in the extended position. Each free end 154 and 156 also includes an outermost free ledge 182*a* and 184*a*, respectively, extending beyond stepped walls 154*a* and 156*a*.

The respiratory component 32 includes first and second clip openings 60, 62 for receiving the intermediate portion 152 of the clip 150. The openings 60, 62 of the respiratory component 32 receive the intermediate portion 152 of the clip 150 whereby the intermediate portion 152 is woven through the openings 60, 62 and passes along an outer wall 186 of the respiratory component 32. The free ends 154, 156 of the clip 150 are woven through the mounting slots 52*a*, 52*c*, 52*d* and 25*e* of the belt 38, whereby the end ledges 182 and 184 project from the outer surface 84 of the belt 38, while the outermost free ledges 182*a* and 184*a* project along the inner face 86 of the belt 38. An example of a suitable respiratory component for use with the mounting clip 150 is JUPITER brand turbo unit (Part No. 085-00-05P) from 3M United Kingdom PLC (Bracknell, UK).

In the embodiment shown in FIG. 16, four of the mounting slots 52*a*, 52*c*, 52*d*, and 52*f* receive the walls 166*a*, 154*a*, 156*a*, and 168*a*, respectively, of free ends 154, 156 of the clip 150. Between each mounting slot 52, one of the two faces (158, 160) of the clip 150 aligns against either the outer face 84 or the inner face 86 of the belt 38. To attach or remove the respiratory component 32 from the belt, the free ends 154, 156 of the clip 150 are inserted into or removed from the mounting slots 52 in the belt 38. At least the free ends 154, 156 of the clip 150 are flexibly resilient to accommodate insertion and removal to and from the mounting slots 52 of the belt 38. The intermediate portion 152 of the clip 150 is sufficiently flexible to weave through the clip openings 60, 62 of the respiratory component 32.

Figure 17:
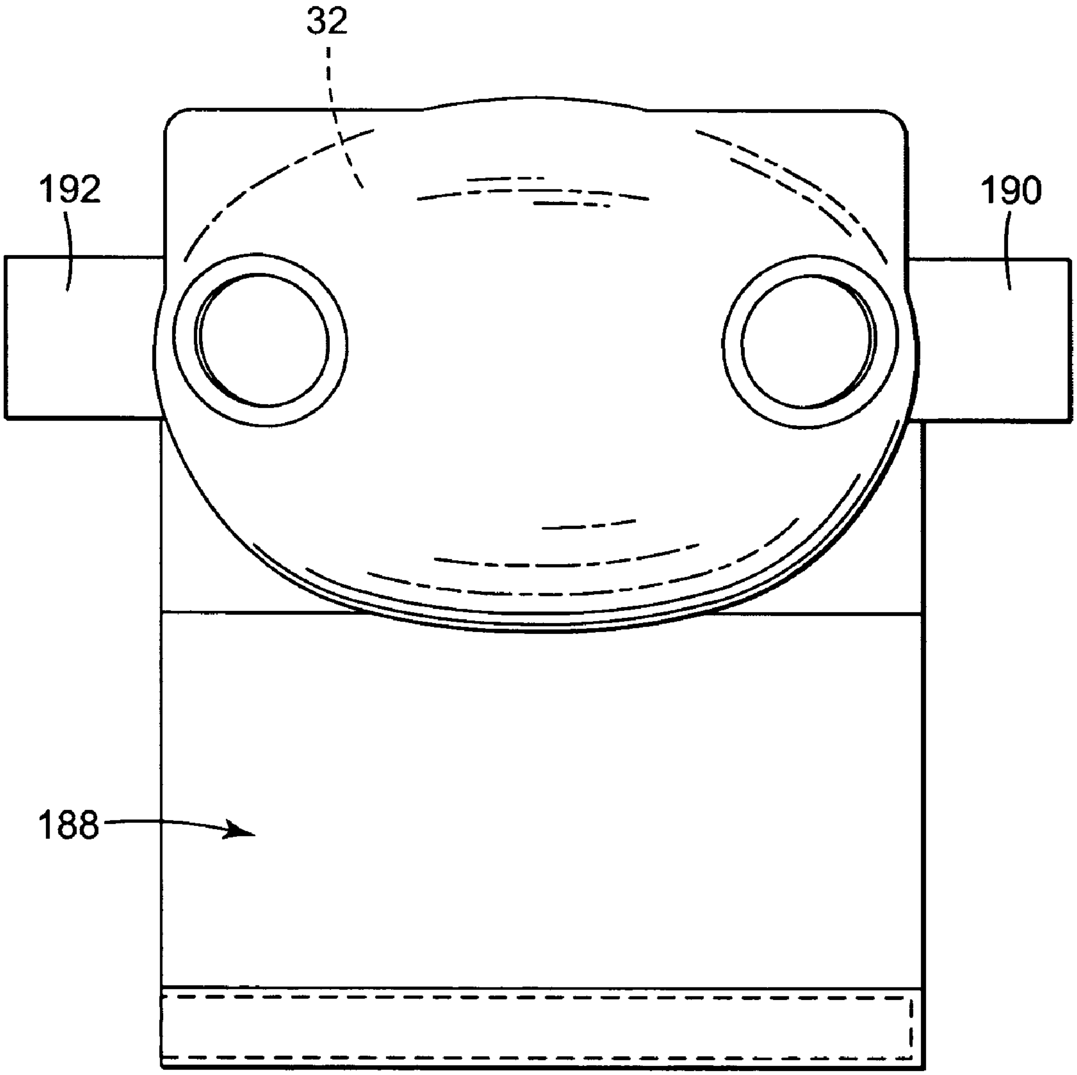
FIG. 17 is a side view of a respiratory component encased in a protective pouch.

The mounting assembly 150 shown in FIGS. 15 and 16 is particularly useful in explosive or dusty environments. As seen in FIG. 16, a protective pouch 188 can be used to encase the respiratory component 32 to keep dust out of the component and/or prevent explosive materials from coming into contact with the component. FIG. 17 is a side view of the respiratory component 32 encased in the protective pouch 188. An example of a suitable protective pouch for use with the mounting clip 150 is JUPITER IS brand battery 4 hr including pouch (Part No. 085-12-00P) from 3M United Kingdom PLC (Bracknell, UK).

The respiratory component 32 is placed in the protective pouch 188 and the intermediate portion 152 of the mounting clip 150 is inserted through the openings 60, 62 on the respiratory component 32. The pouch 158 includes sleeves 190, 192 for free ends 154, 156 of the clip 150 to pass through. The free ends 154, 156 of the mounting clip 150 project through the pouch 188 while the intermediate portion 152 is enclosed within the pouch 188. Because the free ends 154, 156 are received by the belt 38 (rather than the respiratory component 32), the respiratory component 32 is enclosed in the pouch 188, yet still detachable from the belt 38 without exposing the respiratory component 32 to a harmful environment. In further applications of the mounting assembly 150, the respiratory component 32 is not encased in the protective pouch 188.

Figure 19:
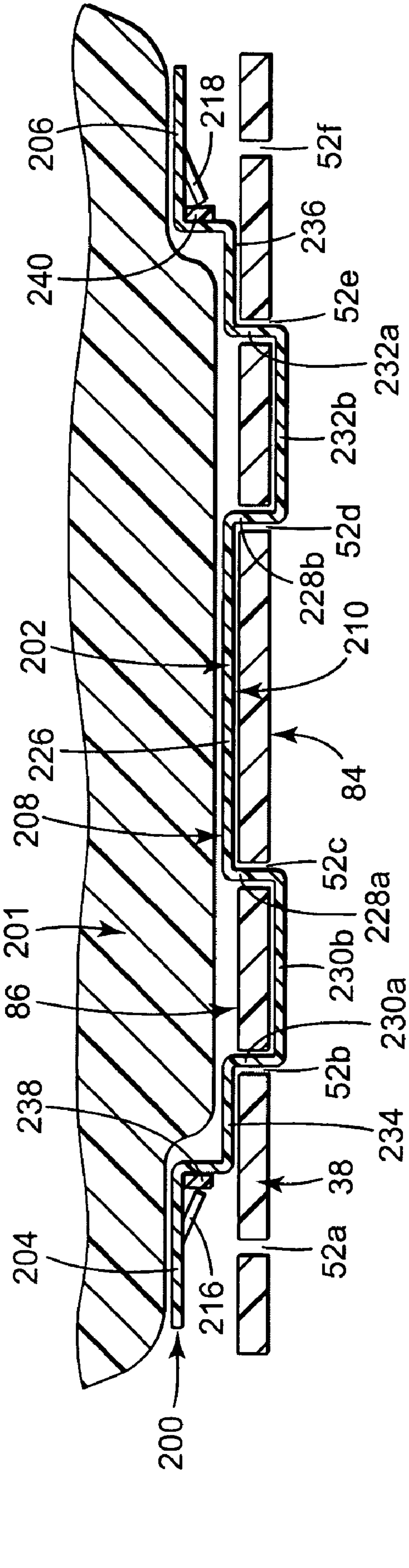
FIG. 19 is a schematic cross-sectional view of the waist-mounted respiratory component system, taken along line A-A of FIG. 10, and including the respiratory component mounting clip of FIG. 18.

FIG. 18 is a perspective view of further embodiment of a mounting clip 200 for attaching a respiratory component 201 to the belt 38 and FIG. 19 is a cross-sectional view of the waist-mounted respiratory component system 48, taken along line A-A of FIG. 10, showing the respiratory component mounting clip 200 and the respiratory component 201 mounted to the inventive belt 38. The mounting clip 200 includes an intermediate portion 202, two spaced apart free ends 204, 206 connected to the intermediate portion 202, a first surface 208 and a second surface 210. The intermediate portion 202 extends between a first shoulder 212 and a second shoulder 214, while the first and second free ends 204, 206 extend from the first and second shoulders 212, 214, respectively. The free ends 204, 206 are aligned to extend in generally opposite directions. The first and second free ends 204, 206 of the mounting clip 200 include first and second biased detent tabs 216, 218 extending generally downwardly and inwardly from the second surface 210 of the mounting clip 200.

The first surface 208 of the intermediate portion 202 defines a channel 220 extending between a first outer wall 222 and a second outer wall 224. The channel 220 includes a stepped portion 226 extending towards the first surface 208 and defining a second channel 228 on the second surface 210 of the mounting clip 200. A depth of the first channel 220 (defined by walls 222 and 224) is greater than a depth of the second channel 228 (defined by walls 228*a* and 228*b*). Formed in the channel 220 are first and second subchannels 230, 232, which extend towards the second surface 210 and are defined on the first surface 208 of the mounting clip 200. A depth of each subchannel 230 (defined by walls 230*a* and 228*a*) and subchannel 232 (defined by walls 232*a* and 228*b*) is substantially equal to the depth of the second channel 228. First and second ledges 234, 236 extend between the first and second subchannels 230, 232 and the first and second outer walls 222, 224, respectively. Ledge 230*b* is in subchannel 230, ledge 232*b* is in subchannel 232, and the stepped portion 226 is in channel 220 and separates subchannels 230 and 232.

The intermediate portion 202 of the clip 200 is woven through the mounting slots 52 of the belt 38, whereby the free ends 204, 206 project from the inner surface 86 of the belt 38. In the embodiment shown in FIG. 18, four of the mounting slots 52*b*, 22*c*, 52*d*, and 52*e* receive walls 230*a*, 228*a*, 228*b*, and 232*a*, respectively, of the intermediate portion 202 of the clip 200. Between each mounting slot 52*a*-52*f*, one of the ledges 234, 230*b*, 226, 232*b*, and 236 of the two faces (208, 210) of the clip 200 aligns against either the outer face 84 or the inner face 86 of the belt 38.

The respiratory component 201 includes first and second openings 60, 62 for removably receiving the free ends 204, 206 of the clip 200. The respiratory component 201 also includes first and second opposed detent surfaces 238, 240 adjacent the first and second clip openings 60, 62, respectively. The openings 60, 62 of the respiratory component 201 receive the free ends 204, 206 of the clip 200 whereby the detent tabs 216, 218 of the clip 200 form a locking engagement with the detent surfaces 238, 240 of the respiratory component 201. To attach or remove the respiratory component 201 from the belt 38, the free ends 204, 206 of the clip 200 are inserted into or removed from the clip openings 60, 62 in the respiratory component 201. Detent tabs 216, 218 are pressed towards the second surface 210 of the clip 200 to facilitate insertion and removal to and from the clip openings 60, 62 of the respiratory component 201. At least the free ends 204, 206 of the clip 200 are flexibly resilient to accommodate insertion and removal to and from the clip openings 60, 62 of the respiratory component 201. The intermediate portion 202 of the clip 200 is sufficiently flexible to weave through the mounting slots 52 of the belt 38. An example of a suitable respiratory component for use with the mounting clip 200 is DUSTMASTER brand air filter unit (Part No. 021-00-38P) from 3M United Kingdom PLC (Bracknell, UK).

In further embodiments of the respiratory component system, the belt 38 includes sufficient mounting slots 52 (or other suitable fasteners or attachment elements) for accommodating more than one mounting assembly 50, and thereby facilitating the attachment of more than one respiratory component to the belt 38. Rather than just attaching a respiratory component at the back section 68 of the belt 38, additional components may attached anywhere along the outer perimeter of the belt 38. In addition, the alignment of the mounting slots 52 of the belt 38 may be other than generally parallel to accommodate differing orientations of mounting clips and connector receptacles on the respiratory components, as well as respiratory components of varying size.

Although the present invention has been described with reference to several embodiments, workers skilled in the art will recognize that changes may be made in form and detail without departing from the spirit and scope of the invention.

The invention claimed is:

1. A belt for use in carrying one or more waist-mounted respiratory protection components, the belt comprising:
- a main belt portion having a back section, a left side section, a left connective section between the back section and the left side section, a right side section and a right connective section between the back section and the right side section wherein the back section is the widest section of the main belt portion,
- wherein the main belt portion is shaped to be secured around a user's pelvic girdle and to distribute a weight of the respiratory component around a pelvis of the user, and further wherein the shape of the main belt portion promotes a sacral angle of the user's pelvis and spine of about 30 degrees;
- a mounting clip attached to the main belt portion for mounting the respiratory component to the main belt portion; and
- a belt buckle portion having a right piece connected to the right side section of the main belt portion and a left piece connected to the left side section of the main belt portion.

2. The belt of claim 1 wherein the mounting clip is releasably attached to the main belt portion.

3. The belt of claim 2 wherein the back section of the main belt portion includes a plurality of slots therein for use in mounting the respiratory component thereon.

4. The belt of claim 3 wherein the mounting clip is woven through at least one of the slots.

5. The belt of claim 1 wherein the left and right side and connective sections are symmetrically shaped relative to the back section, and further wherein each side section has a generally horizontal forward segment and a downwardly angled rearward segment.

6. The belt of claim 1 wherein each connective section of the main belt portion defines a plurality of downwardly and outwardly radiating hinges thereon to facilitate bending in use.

7. The belt of claim 1 wherein the main belt portion has an upper peripheral edge and a lower peripheral edge, and wherein along at least a flared portion of the main belt portion, the lower edge extends outwardly, relative to a user, beyond the upper edge.

8. The belt of claim 7 wherein the main belt portion has a generally conical shape.

9. The belt of claim 7 wherein the flared portion extends along the entire main belt portion.

10. The belt of claim 7 wherein the flared portion includes the right and left side sections.

11. The belt of claim 1 wherein the main belt portion is formed at least partially from a generally rigid material, relative to the right and left pieces of the belt buckle portion.

12. The belt of claim 1 wherein the main belt portion is formed from an ethyl vinyl acetate (EVA) co-polymer.

13. The belt of claim 1 wherein the main belt portion has an outer layer and an inner layer, the outer layer providing rigidity and the inner layer providing a cushioning layer.

14. The belt of claim 13 wherein the inner layer is formed from an ethyl vinyl acetate (EVA) copolymer with a polyolefin elastomer having a density of about 70 $kg/m^3$ to about 75 $kg/m^3$.

15. The belt of claim 13 wherein the outer layer is formed from an ethyl vinyl acetate (EVA) co-polymer with a polyolefin elastomer having a density of about 125 $kg/m^3$.

16. The belt of claim 1 wherein the main belt portion is formed from materials that is readily decontaminatable.

17. The belt of claim 1 wherein the back section of the main belt portion is reinforced.

18. The belt of claim 1 wherein the main belt portion has an inner face and an outer face, and wherein the inner face on the back section has at least one generally vertically disposed air flow channel therein.

19. The belt of claim 1 wherein the main belt portion has an inner face and an outer face, and wherein an inner face of each of the connective sections has a plurality of generally vertically disposed channels therein.

20. The belt of claim 1, and further comprising:

one or more connector elements on the main belt portion for use in mounting additional supportive or respiratory components thereto.

21. The belt of claim 1 wherein at least one of the right and left pieces of the belt buckle portion is adjustable in length.

22. The belt of claim 1 wherein free ends of the right and left pieces of the belt buckle portion are selectively connected together by a releasable buckle.

23. The belt of claim 1 wherein the belt buckle portion is formed from a coated polyester.

24. The belt of claim 23 wherein the polyester is coated with a polyurethane.

25. The belt of claim 23 wherein the polyester is coated with a PVC.

26. The belt of claim 1 wherein the belt buckle portion is releasably connected to the main belt portion.

27. A belt for use in carrying one or more waist-mounted respiratory protection components, the belt comprising:

a main belt portion, the main belt portion having a back section, a left side section, a right side section, a left connective section between the back section and the left side section, and a right connective section between the back section and the right side section, the back section being wider than the other sections of the main belt portion and having a plurality of slots therein for use in mounting a respiratory protection component thereon, the left and right side and connective sections being symmetrically shaped relative to the back section, each side section having a generally horizontal forward segment and a downwardly angled rearward segment; and a belt buckle portion having a right piece connected to the right side section of the main belt portion and a left piece connected to the left side section of the main belt portion, wherein the main belt portion is shaped to be secured around a user's pelvic girdle and to align the respiratory component thereon over the lumbar region of the user's spine at an ideal angle of inclination of approximately 15 degrees, to distribute a weight of the respiratory component around a pelvis of the user, allow free leg movement, minimize pinching adjacent a user's iliac crests during such movement, and shift the rotational momentum of the weight of the respiratory component toward the user, thus further enhancing user comfort.

28. The belt of claim 27 wherein each connective section of the main belt portion defines a plurality of downwardly and outwardly radiating hinges thereon to facilitate bending in use.

29. The belt of claim 27 wherein the main belt portion has an upper peripheral edge and a lower peripheral edge, and wherein along at least a flared portion of the main belt portion, the lower edge extends outwardly, relative to a user, beyond the upper edge.

30. The belt of claim 29 wherein the main belt portion has a generally conical shape.

31. The belt of claim 27 wherein the main belt portion is formed at least partially from a generally rigid material, relative to the right and left pieces of the belt buckle portion.

32. The belt of claim 27 wherein the main belt portion has an outer layer and an inner layer, the outer layer providing rigidity and the inner layer providing a cushioning layer.

33. The belt of claim 27 wherein the main belt portion is formed from materials which are readily decontaminatable.

34. The belt of claim 27 wherein the back section of the main belt portion is reinforced.

35. The belt of claim 27 wherein the main belt portion has an inner face and an outer face, and wherein the inner face on the back section has at least one generally vertically disposed air flow channel therein.

36. The belt of claim 27 wherein the main belt portion has an inner face and an outer face and wherein an inner face of each of the connective sections has a plurality of generally vertically disposed channels therein.

37. The belt of claim 27, and further comprising:

one or more connector elements on the main belt portion for use in mounting additional supportive or respiratory components thereto.

38. The belt of claim 27 wherein at least one of the right and left pieces of the belt buckle portion are adjustable in length.

39. The belt of claim 27 wherein free ends of the right and left pieces of the belt buckle portion are selectively connected together by a releasable buckle.

40. The belt of claim 27 wherein the belt buckle portion is releasably connected to the main belt portion.

* * * * *

UNITED STATES PATENT AND TRADEMARK OFFICE

CERTIFICATE OF CORRECTION

PATENT NO. : 7,454,800 B2
APPLICATION NO. : 10/748907
DATED : November 25, 2008

INVENTOR(S) : David S. Taylor

It is certified that error appears in the above-identified patent and that said Letters Patent is hereby corrected as shown below:

<u>Column 4</u>
Line 58, Delete “spinea” and insert -- spinae --, therefor.

<u>Column 5</u>
Line 40, After “10/749,177” insert -- , --.

<u>Column 7</u>
Line 55, Delete “maybe” and insert -- may be --, therefor.
Line 60, Delete “Luzem,” and insert -- Luzern, --, therefor.

<u>Column 8</u>
Line 2, Delete “decontaminatable” and insert -- decontaminatible --, therefor.
Line 4, Delete “decontaminatable” and insert -- decontaminatible --, therefor.

<u>Column 13</u>
Line 29, Delete “decontaminatable” and insert -- decontaminatible --, therefor.

<u>Column 14</u>
Line 42, Delete “decontaminatable” and insert -- decontaminatible --, therefor.

Signed and Sealed this

Twelfth Day of May, 2009

JOHN DOLL
*Acting Director of the United States Patent and Trademark Office*